United States Patent
Huang et al.

(10) Patent No.: US 8,212,066 B2
(45) Date of Patent: Jul. 3, 2012

(54) PROCESS FOR PRODUCING DIARYL CARBONATES

(75) Inventors: Zhen Wei Huang, Chiayi (TW); Chih Wei Chang, Ta-Sheh (TW); Chia Jung Tsai, Kaohsiung (TW)

(73) Assignee: China Petrochemical Development Corporation, Taipei (TW)

( * ) Notice: Subject to any disclaimer, the term of this patent is extended or adjusted under 35 U.S.C. 154(b) by 205 days.

(21) Appl. No.: 12/813,185

(22) Filed: Jun. 10, 2010

(65) Prior Publication Data

US 2011/0152558 A1 Jun. 23, 2011

(30) Foreign Application Priority Data

Dec. 21, 2009 (TW) ................ 98143851 A

(51) Int. Cl.
*C07C 68/00* (2006.01)

(52) U.S. Cl. ...................... 558/274; 558/260

(58) Field of Classification Search ........... 558/260, 558/270, 274
See application file for complete search history.

(56) References Cited

U.S. PATENT DOCUMENTS

| | | | |
|---|---|---|---|
| 4,096,168 A | 6/1978 | Hallgren | |
| 4,349,485 A | 9/1982 | Hallgren | |
| 4,410,464 A | 10/1983 | Hallgren | |
| 5,132,447 A | 7/1992 | King, Jr. | |
| 5,284,964 A | 2/1994 | Pressman et al. | |
| 5,498,742 A | 3/1996 | Buysch et al. | |
| 5,821,377 A * | 10/1998 | Buysch et al. | 558/274 |
| 6,384,262 B1 * | 5/2002 | Ofori et al. | 558/274 |
| 6,472,551 B2 * | 10/2002 | Ofori et al. | 558/274 |
| 6,521,777 B2 * | 2/2003 | Ofori et al. | 558/274 |
| 6,753,288 B2 * | 6/2004 | Shalyaev et al. | 502/155 |

FOREIGN PATENT DOCUMENTS

| | | |
|---|---|---|
| EP | 0 350 700 A2 | 1/1990 |
| JP | 4-257546 A | 9/1992 |
| JP | 8-325207 A | 12/1996 |

* cited by examiner

*Primary Examiner* — Golam M M Shameem

(74) *Attorney, Agent, or Firm* — Sughrue Mion, PLLC

(57) ABSTRACT

The present invention relates to a process for producing diaryl carbonates, which is to synthesize diaryl carbonates by oxidative carbonylation of phenols with carbon monoxide and oxygen, and in particular, to synthesize diphenyl carbonate from phenol. The present invention is characterized in that a catalytic system comprising a metal halide catalyst and one or more cocatalysts of nitrogenous heterocyclic compounds is used to increase the convertibility, selectivity and yield of this catalytic reaction.

14 Claims, No Drawings

PROCESS FOR PRODUCING DIARYL CARBONATES

FIELD OF THE INVENTION

The present invention relates to a process for producing diaryl carbonates, which is to synthesize diaryl carbonates by oxidative carbonylation of phenols with carbon monoxide and oxygen, and in particular, to synthesize diphenyl carbonate from phenol.

BACKGROUND TO THE INVENTION

Diphenyl carbonate (DPC) is a less-toxic and contamination-free organic substance and an intermediate of important engineering plastic materials, and can be used in the synthesis of many important organic compounds and macromolecule materials, such as monoisocyanates, diisocyanates, polycarbonates, methyl parahydroxybenzoates, poly(aryl carbonates), etc., and as a plasticizer and solvent for polyamides and polyesters.

Recently, with the development in non-phosgene synthesis of high quality polycarbonate (PC) by using diphenyl carbonate and bisphenol A as the raw materials, diphenyl carbonate becomes a most attention-getting compound. The production of polycarbonate mostly adopts the method of polymerizing bisphenol A with phosgene or methyl chloroformate in a two-phase system of methylene chloride-water (also known as Interfacial Polymerization); however, phosgene and methyl chloroformate are very toxic substances, which will contaminate the environment severely and corrode the equipment. On the contrary, the synthesis of polycarbonate from diphenyl carbonate can avoid using toxic solvents and chlorine-containing materials so as to reduce the corrosion of equipment and contamination of environment.

Currently, there are three main methods to synthesize diphenyl carbonate: the phosgene method, the ester exchange method and the method of oxidative carbonylation of phenol. The phosgene method is the earliest method and also the main method for producing diphenyl carbonate in the past. However, this method is complex in its process, high in cost and poor in quality, and the phosgene is very toxic and contaminates the environment severely. Thus, in foreign countries, the phosgene method has been weeded out. The ester exchange method uses dimethyl carbonate (U.S. Pat. No. 4,410,464) or dimethyl oxalate (JP 08-325207) so as to avoid the use of phosgene; however, its equilibrium conversion is low, the recovery of homogenous catalysts is difficult and it requires special reaction equipment. The method of oxidative carbonylation of phenol uses carbon monoxide, oxygen, phenol directly to synthesize diphenyl carbonate in one step. This method has a simple process, uses cheap raw materials and does not contaminate the environment, which is an attractive process route and is well worth further developing and researching.

U.S. Pat. No. 4,096,168 of General Electric Company discloses a diaryl carbonate process, comprising phenol, carbon monoxide, a base, and a Group VIIIB metal compound having an oxidation state greater than zero used as the catalyst, wherein said base is a sterically hindered amine. U.S. Pat. No. 4,096,169 also discloses that this reaction system can be carried out in the absence of any solvent, when phenols play a dual role of reactant and solvent, or in the presence of a solvent, and a suitable solvent can be methylene chloride, toluene, diphenylether, chlorobenzene, o-dichlorobenzene, etc. In addition, the base in the catalytic system can be an organic or inorganic base, such as alkali metals or alkaline earth metals and their hydroxides, quaternary ammonium and phosphonium, primary, secondary or tertiary amines, etc. Because this catalytic system cannot be re-oxidized to its original oxidation number after the oxidation state of the Group VIIIB metal having an oxidation state greater than zero reduces to zero as the reaction carries out, the reaction terminates. Also, this process uses organic solvents, which may cause contamination.

U.S. Pat. No. 4,349,485 discloses a diaryl carbonate process, comprising phenol, carbon monoxide, a base and a Group VIIIB metal, and further comprising an oxidant and a redox co-catalyst of manganese tetradentates. The manganese tetradentates are of the formula $(L)_x Mn$ wherein L is bis(β-diketone) ($C_{14-20}H_{22-34}O_4$), the oxidant is air, and a molecular sieve and tetrabutylammonium bromide are used as the drying agent and the phase transfer agent, respectively. The reaction time of this process is 80 hr and the convertibility of phenol is about 50%, which reactivity is too low.

U.S. Pat. No. 5,132,447 discloses the use of a homogenous catalytic system of palladium (II) acetate/cobalt (II) diacetate/tetra-n-butylammonium bromide, with benzoquinone added, to increase the yield of diphenyl carbonate from 15.2% to 26.1% at a high pressure (the maximum pressure is up to 2050 psi). U.S. Pat. No. 5,284,964 discloses the finding that the yield of diphenyl carbonate can achieve 45% by using palladium (II) acetate as the main catalyst, cobalt di-(salicylal)-3,3'-diamino-N-methyldipropylamine (CoSMDPT) as the inorganic cocatalyst, tetraalkylammonium bromide or hexaalkylguanidinium bromide as the source of bromides in the presence of the organic cocatalyst of terpyridine and introducing carbon monoxide and oxygen in a fixed ratio at a high pressure (the maximum pressure is up to 1600 psi). In order to achieve commercially acceptable reaction rate and selectivity, this process must be carried out at a high pressure. However, under the condition that the total reaction pressure increases continuously, the equipment investment cost will be increased greatly when commercialization.

EP 350,700 uses a cobalt salt as the inorganic cocatalyst with a quinine or hydroquinone added as the electron transfer catalyst. However, in this process, the removal of electron transfer catalyst is extremely costly. The two OH groups provided by hydroquinone will also cause the phenol to form byproducts of carbonates, and the removal of such byproducts is costly. Also, the electron transfer catalyst cannot be recovered for reuse and the formation of byproducts lowers the selectivity. Thus the economic burden increases.

The process disclosed by JP 04-257546 is carried out in a distillation tower, which uses noble metals and quaternary salts as the catalytic system and removes reaction water by distillation. Due to the equipment problem, the holdup time is very short so that the space-time yield (STY) is very low and is merely 17.8 g/1 h. Also, a large amount of halogen ions exist in the catalytic system used by this process, which will cause corrosion.

U.S. Pat. No. 5,498,742 uses palladium bromide/tetrabutylammonium bromide/manganese(II) acetylacetonate/sodium phenolate as the catalytic system. However, the catalyst should be activated with a large amount of carbon monoxide first, which is not economically beneficial.

SUMMARY OF THE INVENTION

In view of the aforementioned problems, the main object of the present invention is to provide a process for producing diaryl carbonates, which has high reaction convertibility at a low reaction pressure.

Another object of the present invention is to provide a process for producing diaryl carbonates, which has high reaction selectivity.

Yet another object of the present invention is to provide a process for producing diaryl carbonates, which has high reaction convertibility.

Yet another object of the present invention is to provide a process for producing diaryl carbonates, which has high reactivity.

The process for producing diaryl carbonates according to the present invention is to synthesize diaryl carbonates by oxidative carbonylation of phenols with carbon monoxide and oxygen in the presence of a catalytic system comprising Group VIIIB metal halides in combination with one or more nitrogenous heterocyclic compounds as the organic cocatalyst.

In particular, the present invention is to synthesize diphenyl carbonates by oxidative carbonylation, in which a catalytic system comprising a palladium halide catalyst in combination with one or more nitrogenous heterocyclic compounds as the organic cocatalyst is used to catalyze phenol.

The process for producing diaryl carbonates according to the present invention is characterized in that the medium for oxidative carbonylation comprises the following components: (1) a metal halide catalyst, (2) phenol, (3) a base, (4) an inorganic cocatalyst, (5) a quaternary ammonium halide, (6) carbon monoxide, (7) oxygen, and (8) an organic cocatalyst. The metal halide catalyst can be palladium halide such as, for example, palladium chloride. The organic cocatalyst can be one or more nitrogenous heterocyclic compounds represented by the following formula:

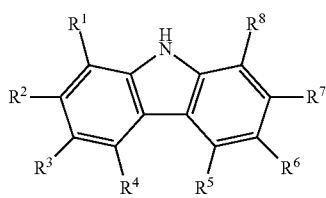

In the formula, $R^1$-$R^8$ each is independently a hydrogen atom; a straight or branched chain $C_{1-12}$ alkyl group; a $C_{3-12}$ cycloalkyl group; a $C_{7-12}$ arylalkyl group; a $C_{6-12}$ aryl group; a $C_{7-12}$ alkylaryl group; a halogen atom; a nitro group; a cyano group; an amino group; a $C_{1-10}$ alkyl group, $C_{7-10}$ arylalkyl group, $C_{3-10}$ cycloalkyl group, $C_{6-10}$ aryl group or $C_{7-10}$ alkylaryl group containing O, S, N or a carboxyl group; or a salt group containing O, S, N or a carboxyl group.

In particular, the organic cocatalyst is a nitrogenous heterocyclic compound of carbazoles, and the examples of the organic cocatalyst of carbazoles include, but are not limited to, carbazole, 3,6-dichlorocarbazole, 3,6-dibromocarbazole, 2-acetylcarbazole and 2-hydroxybenzo[a]carbazole-3-carboxylic acid sodium salt.

According to the present invention, the catalytic system is composed of a metal halide, especially palladium halide, and one or more nitrogenous heterocyclic compounds as the organic cocatalyst, and diphenyl carbonate is synthesized from phenol by carrying out the oxidative carbonylation in a 1 L high pressure reactor. The reaction temperature is 60-140° C., and preferably 70-100° C.; the reaction pressure is 5-80 kg/cm², and preferably 6-12 kg/cm²; the molar ratio of the cocatalyst to the catalyst is 10:1 to 1:10, and preferably 5:1 to 1:5; and the metal concentration of the catalyst is 100-8000 ppm, and preferably 200-2000 ppm.

The features and effects of the present invention will be further explained with reference to the preferred embodiments below, which are, however, not intended to restrict the scope of the present invention.

DESCRIPTION OF PREFERRED EMBODIMENTS

The convertibility, selectivity and yield used in the specification are calculated according to the following equations:

Convertibility (%)=Amount of Consumed Phenol (mol)/Amount of Added Phenol (mol)×100%

Selectivity (%)=2×Amount of Produced DPC (mol)/Amount of Consumed Phenol (mol)×100%

Yield (%)=Convertibility (%)×Selectivity (%)×100%

COMPARATIVE EXAMPLE

In a 1 L stainless steel high pressure reactor with stirrer, 231.72 g (2.4 mol) of phenol, 0.35 g (0.00139 mol) of manganese acetylacetonate, 3.87 g (0.012 mol) of tetrabutylammonium bromide and 0.35 g (0.00878 mol) of sodium hydroxide were added. A catalyst of palladium chloride was added so that the amount of palladium was 265 ppm based on the total amount of reactants. The air in the reactor was replaced with a mixed gas of carbon monoxide and oxygen, followed by starting the stirrer to pressurize the reactor to 10 kg/cm² and elevate the temperature of the reaction system to 80° C. The volume ratio of oxygen/carbon monoxide was 5/95 during the reaction, and the pressure of the reactor was kept at 10 kg/cm². Samplings were conducted at 60 minutes after the reaction was initiated. The samples were analyzed with gas chromatography. The result is shown in Table 1.

Examples 1-5

The steps of the Comparative Example were repeated except that different organic cocatalysts were added and the molar ratio of the organic cocatalyst to the catalyst was 1:1. The results are shown in Table 1. It is shown that, in a certain extent, the yields are all increased when the palladium chloride catalyst is used in combination with different cocatalysts.

TABLE 1

The benefit of palladium chloride in combination with different cocatalysts to the improvement on the yield of diphenyl carbonate

| | Cocatalyst | Convertibility (%) | Selectivity (%) | Yield (%) |
|---|---|---|---|---|
| CEx. | none | 5.9 | 98.9 | 5.8 |
| Ex. 1 | carbazole | 7.2 | 100.0 | 7.2 |
| Ex. 2 | 3,6-dibromocarbazole | 10.3 | 99.1 | 10.2 |
| Ex. 3 | 3,6-diaminocarbazole | 10.4 | 100.0 | 10.4 |
| Ex. 4 | 2-acetylcarbazole | 8.4 | 99.3 | 8.3 |
| Ex. 5 | 2-hydroxybenzo[a]carbazole-3-carboxylic acid sodium salt | 9.0 | 99.3 | 8.9 |

CEx. = Comparative Example
Ex. = Example

Examples 6-7

The steps of the Comparative Example were repeated except that palladium chloride was used in different concentrations and the cocatalyst of 3,6-dibromocarbazole was used in a molar ratio of 1:1 with respect to the catalyst. The results are shown in Table 2. It is shown that the cocatalyst will benefit the production of diphenyl carbonate under different concentrations of the palladium chloride catalyst.

TABLE 2

The influence of the cocatalyst on the synthesis of diphenyl carbonate under different concentrations of palladium halide

|  | Pd concentration (ppm) | Convertibility (%) | Selectivity (%) | Yield (%) |
| --- | --- | --- | --- | --- |
| Ex. 2 | 265 | 10.3 | 99.1 | 10.2 |
| Ex. 6 | 132 | 7.0 | 99.1 | 6.9 |
| Ex. 7 | 1000 | 6.8 | 98.9 | 6.7 |

Ex. = Example

Example 8

The steps of the Comparative Example were repeated except that the reaction was carried out at a different reaction pressure and the cocatalyst as used was 3,6-dibromocarbazole. The result is shown in Table 3. It is shown that, with the use of the cocatalyst of the present invention, a higher yield than that of the original system can still be obtained at different pressures.

TABLE 3

The influence of pressure on the production of diphenyl carbonate

|  | Reaction pressure (kg/cm$^2$) | Convertibility (%) | Selectivity (%) | Yield (%) |
| --- | --- | --- | --- | --- |
| Ex. 2 | 10 | 10.3 | 99.1 | 10.2 |
| Ex. 8 | 8 | 6.5 | 98.8 | 6.4 |

Ex. = Example

Example 9

The steps of the Comparative Example were repeated except that the reaction was carried out at a different reaction temperature and the cocatalyst as used was 3,6-dibromocarbazole. The result is shown in Table 4. It is shown that, with the use of the cocatalyst of the present invention, a higher yield than that of the original system can still be obtained at relatively-higher temperatures.

TABLE 4

The influence of temperature on the production of diphenyl carbonate

|  | Reaction temperature (° C.) | Convertibility (%) | Selectivity (%) | Yield (%) |
| --- | --- | --- | --- | --- |
| Ex. 2 | 80 | 10.3 | 99.1 | 10.2 |
| Ex. 9 | 90 | 7.5 | 99.0 | 7.4 |

Ex. = Example

Examples 10-11

The steps of the Comparative Example were repeated except that the reaction was carried out with different molar ratios of the cocatalyst to the catalyst and the cocatalyst as used was 3,6-dibromocarbazole. The results are shown in Table 5. It is shown that a higher yield of diphenyl carbonate than that of the original system can still be obtained under different molar ratios of the cocatalyst to the catalyst

TABLE 5

The influence of the ratio between the cocatalyst and the Pd catalyst on the production of diphenyl carbonate

|  | Cocatalyst/Pd catalyst | Convertibility (%) | Selectivity (%) | Yield (%) |
| --- | --- | --- | --- | --- |
| CEx. | no cocatalyst added | 5.9 | 98.9 | 5.8 |
| Ex. 2 | 1/1 | 10.3 | 99.1 | 10.2 |
| Ex. 10 | 1/2 | 7.2 | 99.1 | 7.1 |
| Ex. 11 | 2/1 | 7.9 | 99.2 | 7.8 |

CEx. = Comparative Example
Ex. = Example

What is claimed is:

1. A process for producing a diaryl carbonate, in which the diaryl carbonate is synthesized by oxidative carbonylation of a phenol with carbon monoxide and oxygen, characterized in that a catalytic system comprising a metal halide catalyst and one or more cocatalysts of nitrogenous heterocyclic compounds is used.

2. The process according to claim 1, wherein the metal halide catalyst is a palladium halide.

3. The process according to claim 1 or 2, wherein the cocatalyst is one or more nitrogenous heterocyclic compounds represented by the following formula:

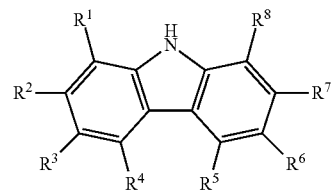

in which R1-R8 each is independently a hydrogen atom; a straight or branched chain C1-12 alkyl group; a C3-12 cycloalkyl group; a C7-12 arylalkyl group; a C6-12 aryl group; a C7-12 alkylaryl group; a halogen atom; a nitro group; a cyano group; an amino group; a C1-10 alkyl group, C7-10 arylalkyl group, C3-10 cycloalkyl group, C6-10 aryl group or C7-10 alkylaryl group containing O, S, N or a carboxyl group; or a salt group containing O, S, N or a carboxyl group.

4. The process according to claim 3, wherein the cocatalyst is a carbazole compound selected from the group consisting of carbazole, 3,6-diaminocarbazole, 3,6-dibromocarbazole, 2-acetylcarbazole and 2-hydroxybenzo[a]carbazole-3-carboxylic acid sodium salt.

5. The process according to claim 1, wherein the molar ratio of the cocatalyst to the catalyst is 10:1 to 1:10.

6. The process according to claim 5, wherein the molar ratio of the cocatalyst to the catalyst is 5:1 to 1:5.

7. The process according to claim 1, wherein the metal concentration of the catalyst is 100-8000 ppm.

8. The process according to claim 7, wherein the metal concentration of the catalyst is 200-2000 ppm.

9. The process according to claim 1, wherein the reaction is carried out at a temperature of 60-140° C.

10. The process according to claim 9, wherein the reaction is carried out at a temperature of 70-100° C.

11. The process according to claim 1, wherein the reaction is carried out at a pressure of 5-80 kg/cm$^2$.

12. The process according to claim 11, wherein the reaction is carried out at a pressure of 6-12 kg/cm$^2$.

13. The process according to claim 2, wherein the cocatalyst is one or more nitrogenous heterocyclic compounds represented by the following formula:

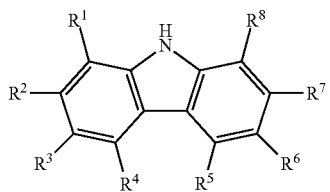

in which R1-R8 each is independently a hydrogen atom; a straight or branched chain C1-12 alkyl group; a C3-12 cycloalkyl group; a C7-12 arylalkyl group; a C6-12 aryl group; a C7-12 alkylaryl group; a halogen atom; a nitro group; a cyano group; an amino group; a C1-10 alkyl group, C7-10 arylalkyl group, C3-10 cycloalkyl group, C6-10 aryl group or C7-10 alkylaryl group containing O, S, N or a carboxyl group; or a salt group containing O, S, N or a carboxyl group.

14. The process according to claim 13, wherein the cocatalyst is a carbazole compound selected from the group consisting of carbazole, 3,6-diaminocarbazole, 3,6-dibromocarbazole, 2-acetylcarbazole and 2-hydroxybenzo[a]carbazole-3-carboxylic acid sodium salt.

* * * * *